United States Patent [19]

Reuss

[11] Patent Number: 5,015,408

[45] Date of Patent: May 14, 1991

[54] DENTURE CLEANING TABLET CONTAINING A BLEACH ACTIVATOR AND AN ORGANIC PHOSPHONIC ACID STABILIZER

[75] Inventor: Mira Reuss, Mannheim, Fed. Rep. of Germany

[73] Assignee: Reckitt GmbH, Fed. Rep. of Germany

[21] Appl. No.: 323,865

[22] Filed: Mar. 15, 1989

[30] Foreign Application Priority Data

Mar. 19, 1988 [DE] Fed. Rep. of Germany ....... 3809359
Apr. 16, 1988 [DE] Fed. Rep. of Germany ....... 3812693

[51] Int. Cl.$^5$ .......................... C11D 7/12; C11D 7/18; C11D 7/36; C11D 17/00
[52] U.S. Cl. ......................................... 252/99; 8/525; 252/103; 252/157; 252/174; 252/174.14; 252/174.16; 252/174.19; 252/186.3; 252/186.38; 252/350; 252/558; 252/DIG. 17; 424/53
[58] Field of Search ...................... 106/35; 252/174.16, 252/DIG. 17, 99, 103, 157, 174, 174.14, 174.19, 186.3, 186.38, 350, 550; 8/525; 424/53

[56] References Cited

U.S. PATENT DOCUMENTS

| 2,765,279 | 10/1956 | Nüsslein et al. | 252/117 |
| 4,054,598 | 10/1977 | Blum et al. | 260/502.5 |
| 4,179,391 | 12/1979 | Kaufmann et al. | 252/99 |
| 4,181,621 | 1/1980 | Raaf et al. | 252/102 |
| 4,499,001 | 2/1985 | Eoga | 252/99 |
| 4,540,504 | 9/1985 | Eoga | 252/99 |
| 4,851,146 | 7/1989 | Hosoi et al. | 252/102 |

FOREIGN PATENT DOCUMENTS

| 0010412 | 4/1980 | European Pat. Off. |
| 0102418 | 3/1984 | European Pat. Off. |
| 0133354 | 2/1985 | European Pat. Off. |
| 0149308 | 7/1985 | European Pat. Off. |
| 0157464 | 10/1985 | European Pat. Off. |
| 0225658 | 6/1987 | European Pat. Off. |
| 0253772 | 1/1988 | European Pat. Off. |
| 3247893 | 6/1984 | Fed. Rep. of Germany |
| 1075470 | 7/1967 | United Kingdom |

OTHER PUBLICATIONS

*Kirk-Othmer Encyclopedia of Chemical Technology*, vol. 5, 1964, pp. 865, 866 and 871.

*Primary Examiner*—Paul Lieberman
*Assistant Examiner*—A. Beadles-Hay
*Attorney, Agent, or Firm*—Hill, Van Santen, Steadman & Simpson

[57] ABSTRACT

Cleaning tablet for the automatic cleaning of dentures in an aqueous solution, with a content of sodium hydrogen carbonate and/or sodium carbonate or carbonates, citric acid or citrate or citrates, sodium perborate, potassium monopersulphate, surfactants and foam forming agents, binders, lubricants and disintegrants, antimicrobial agents, carriers, flavoring/aromatizing substances, at least one perborate/peroxide activator and at least one phosphorus compound, characterized in that the activator content is between 0.5 and 3.0% by weight of the total composition of the cleaning tablet, is the phosphorus compound is includes at least one hydrolysis-stable organic phosphonic acid and/or a salt thereof that acts as a stabilizing agent and having a content between 0.5 and 3.0% by weight of the total composition of the cleaning tablet and that the total composition of the cleaning tablet is free from inorganic phosphates/polyphosphates and organic sequestrants based on aminocarboxylic acids and hydrophobic binders.

18 Claims, No Drawings

DENTURE CLEANING TABLET CONTAINING A BLEACH ACTIVATOR AND AN ORGANIC PHOSPHONIC ACID STABILIZER

BACKGROUND OF THE INVENTION

The invention relates to a cleaning tablet for the automatic cleaning of dentures in an aqueous solution having a content of sodium hydrogen carbonate and/or sodium carbonate or carbonates, citric acid or citrate or citrates, sodium perborate, potassium monopersulphate, surfactants and foam forming agents, binders, lubricants and disintegrants, antimicrobial agents, carriers, flavoring/aromatizing substances, at least one perborate/peroxide activator and at least one phosphorous compound.

Denture cleaning tablets, for example of the type described in DE-OS 21 33 710, are used in such a way that they are placed in water at the same time as the denture to be cleaned. When so placed in water the cleaning tablet disintegrates with a more or less pronounced evolution of gas and releases active substances, which attack and remove the contaminant coatings adhering to the denture.

Such cleaning tablets, such as those forming the subject matter of German patent Nos. 23 12 847, 25 48 469, 26 58 450 and 27 41 072, European patent Nos. 0010 412, 0 028 005 and 0 102 418, as well as EP-OS Nos. 0 133 354, 0 149 308, 0 157 464 and 0 225 658, essentially contain oxygen-delivering substances for oxidizing and disinfecting (such as monopersulphates and/or perborates), inorganic softeners and lime binding agents (such as phosphates and/or polyphosphates), chelating agents, such as EDTA, gas-forming carriers, such as carbonates and/or bicarbonates, citric acid, tartaric acid, amidosulphonic acid or their salts, disinfectants, such as benzoates and/or alkyl hydroxybenzoates, as well as lubricants, binders and/or disintegrants, surfactants, colourants and finally flavouring/aromatizing agents. As a function of the composition, when they dissolve in water the pH-values fluctuate between acid, neutral and alkaline. These tablets are generally rapid cleaning tablets; having a cleaning time of 10 to 15 minutes. However, in certain cases they are slow acting tablets having relatively long use periods, in which the full cleaning action with respect to the denture being treated therein is only achieved after roughly 1 to 2 hours.

With respect to the cleaning of dentures, all the aforementioned tablets suffer a disadvantage which is typical for the composition and use practice. The formation of the perborate oxygen in the desired active form via the HOO-ion only takes place in a satisfactory manner at temperatures above 60° C. However, generally dentures are cleaned by the user in 10 to 15 minutes at roughly 30° to 40° C., so that in the case of the known cleaning tablets a considerable part of the intended oxidizing and disinfecting action of the oxygen-delivering substances is not brought about.

EP-OS No. 0 253 772 discloses a cleaning tablet of the aforementioned type, in which the phosphorus compound is constituted by a phosphate combination, which assists or participates in the cleaning process, whilst polymeric fluorocarbon is used as the binder. When using such a hydrophobic fluorocarbon, however, presents a problem. Due to the hydrophobic nature of the cleaning tablet not only is dissolving the tablet made more difficult, but also it floats in the dissolved cleaning liquid in a reactant-separating manner and therefore delays the cleaning action. The use of such a polymeric, hydrophobic binder demonstrates why in the case of the cleaning tablet of EP-OS No. 0 253 772, a high activator content of 5 to 15% by weight is used, which leads to a loss of content of the actual cleaning-specific, active substances. As stated, in the known cleaning tablet, use is also made of inorganic phosphates, which in the same way as the EDTA used act as a metal bonding agent, but are not unobjectionable due to possible environmental influences.

SUMMARY OF THE INVENTION

The present invention provides a so-called fast cleaning tablet of the aforementioned type which, while ensuring the stability and activity of the cleaning tablet by means of a suitable process stabilizing agent, makes it unnecessary to use a hydrophobic binder that does not participate in the cleaning process, or environmentally prejudicial inorganic polyphosphates, EDTA/NTA and NLS.

To this end, a cleaning tablet is provided having an activator content of between approximately 0.5 to about 3.0% by weight of the total composition of the cleaning tablet. In the cleaning tablet, for the phosphorus compound that is exclusively used is at least one hydrolysis-stable organic phosphonic acid and/or a salt thereof acting as a stabilizing agent and with a content between approximately 0.5 to about 3.0% by weight of the total composition of the cleaning tablet. The total composition of the cleaning tablet is free from inorganic phosphates/polyphosphates and organic sequestrants based on aminocarboxylic acids.

In an embodiment, tetraacetyl ethylene diamine (TAED) is used as an activator.

In an embodiment, a dye system is provided having at least two dyes, at least one of the dyes is present in the ketoform coloured with chromophoric groups and as a result of the hydrogen ions released during cleaning, changes into a colourless, desmotropic leuco-enol form, and at least one dye is a redox-neutral. In a preferred embodiment, the dye system includes a combination of sodium-indigotin disulphonate and sodium quinophthalone disulphonate.

In an embodiment, the dye system content with respect to the total composition of the cleaning tablet is between approximately 0.05 to about 0.35% by weight.

In an embodiment, the pH-value of a cleaning liquid produced by dissolving the cleaning table of the present invention in water is between approximately 7.6 to about 9.6.

In an embodiment, the phosphorus compound content of the total cleaning tablet composition is between approximately 0.5 to about 2.5% by weight.

DETAILED DESCRIPTION OF THE PRESENTLY PREFERRED EMBODIMENTS

The present invention provides an improved fast cleaning dental cleaning tablet. The present invention is based on the surprising finding that it is possible to overcome the aforementioned problems of known cleaning tablets. To this end, use is made of an organic phosphonic acid as the metal bonding agent and for stabilizing the peroxide, while obviating the need for a hydrophobic, polymeric binder. It simultaneously constitutes a hydrolysis-stable sequestrant, e.g. for alkali metals and heavy metals and also replaces the environmentally problematical phosphates/polyphosphates and EDTA, which have constituted the inorganic sequestrants in the heretofore known denture cleaning agents. On dissolving the cleaning tablet the peroxide is not impeded by an inert polymer and is instead stabilized by a substance in the cleaning tablet, which after dissolving in the cleaning process has the effect of removing the contact poisons and the like present in the water, so as to keep the activator action in system-imminent manner free from negative influences. According to the present invention it is merely necessary to have an activator content of 0.5 to about 3.0% by weight, so that it is possible to increase the cleaning tablet percentage of active substances. This is also made possible by the fact that in the cleaning tablet according to the present invention, due to the high activator activity, 5 to 10 parts of polyphosphates as is conventionally used in the prior art cleaning tablets, can be replaced by only 1 part of phosphonates. Because the peroxide and activator have a full action in the cleaning liquid, without any "extraneous material" e.g. in the form of hydrophobic polymers floating therein, this ensures that the full activity of the peroxide is maintained over the entire cleaning period of, e.g. 15 minutes, despite the slowly decreasing cleaning liquid temperature in the water glass or the like.

In a preferred embodiment of the present invention tetraacetyl ethylene diamine (TAED) is used as the activator. This makes it possible to considerably increase and stabilize the delivery of active oxygen in the form desired for the cleaning and antimicrobial action via the formation of highly active peracetic acid.

Pursuant to the present invention hydrolysis-stable, organic phosphoric acids, or their salts, are used, which have an increased lime, metal and in particular iron-bonding action and simultaneously have a dispersing-/deflocculating action. In an embodiment of the present invention, a dye system is used. The cleaning tablet with the dye system provides the possibility of optically displaying the cleaning sequence up to the end of the main cleaning and also the overall cleaning process. In this embodiment, during the cleaning process, there is a quantitative reduction of the colour intensity, followed by a qualitative colour change, before decolouring occurs.

It is a characteristic of the cleaning tablet of the present invention that it contains no environmentally prejudicial, inorganic phosphates, polyphosphates and organic sequestrants based on aminocarboxylic acids (e.g. EDTA). The cleaning and antimicrobial action is temperature-insensitive in the use range, i.e. the tablet can be used with an optimum cleaning action in the range approximately 25° C. to approximately 45° C.

As a result of the perborate activator used in the cleaning tablet according to the present invention, a reaction mechanism is initiated in the aqueous solution which can be represented in simplified form as follows:

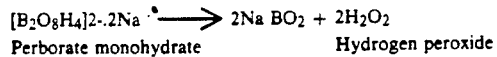
Perborate monohydrate          Hydrogen peroxide   (a)

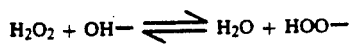   (b)

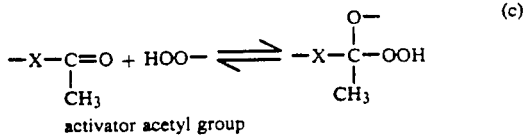
activator acetyl group   (c)

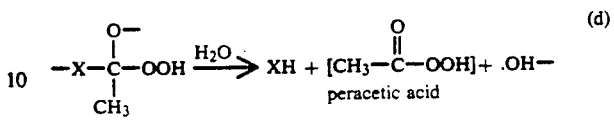
peracetic acid   (d)

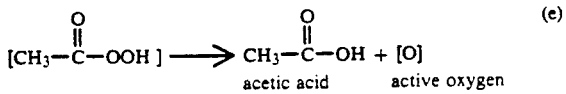
acetic acid    active oxygen   (e)

It is important that peracetic acid is formed as an intermediate stage, which then decomposes into acetic acid and oxygen. The thus activated oxygen delivery of the perborate leads to a significantly improved cleaning action.

The antimicrobial action of the cleaning tablet of the present invention achieved via the perborate/peroxide activator, with peracetic acid as the intermediate stage, also exceeds expectations. It has been found that even in the case of high dilutions and within short action times sterility is obtained. The specific composition of the cleaning tablet can be varied in a manner known to the those skilled in the art in accordance with the intended aims. By way of example, however, the composition will be set forth. In order to obtain after incubating for 48 hours bacteria-free cultures, in the case of a peracetic acid concentration of 0.002 to 0.005% by weight it is sufficient to have an action time of 2 to 10 minutes with respect to conventional test bacteria (*Escherichia coli, Staphylococcus aureus, Streptococcus mutans, Pseudomonas aeruginosa, Proteus vulgaris, Bacillus mesenterieus*), in order to kill them. The same applies with regards to hyphomycetes and blastomycetes (*Trichophyton rubrum, Candida albicans*). Even in the case of the known resistant enteroviruses, when using the inventive cleaning tablet a much lower concentration is required due to the peracetic acid present than in the case of the hitherto used $H_2O_2$.

Whereas the formulations of most known cleaning agents for dentures contain inorganic phosphates and polyphosphates for lime binding and dispersing, as well as organic sequestrants based on aminocarboxylic acid, such as EDTA and NTA, the cleaning tablet according to the present invention requires no such additives. This is advantageous, because polyphosphates are hydrolysis-sensitive, i.e. they hydrolyze in aqueous solution accompanied by the formation of orthophosphates and consequently lose their dispersing action, while EDTA has no dispersing action from the outset. It must also be borne in mind that inorganic phosphates and, e.g. EDTA are not environmentally unobjectionable, because problems are caused by one of these due to the enrichment of the receiving water with oxygen-consuming plants and the other due to their difficult degradability.

In the cleaning tablets of the present invention, the aforementioned, environmentally problematical product groups are kept out of the overall composition. The highly effective lime and metal bonding agents in the form of organic sequestrants based on phosphonic acid or salts thereof used for the first time in the denture cleaning tablets according to the present invention are hydrolysis-stable, have a corrosion-inhibiting action and improve the cleaning process in that, in synergistic cooperation with the perborate activator, they stabilize the oxygen delivering agent or delivery and simultaneously have good dispersing and deflocculating properties.

Substantially all known, commercially available cleaning tablets for dentures prescribe the use of warm water and some water at up to 50° C. for the cleaning liquid. This is necessary with most conventional formulations, in order to dissolve in a desirable time the active oxygen of the peroxide. However, this results in other disadvantages, e.g. a faster hydrolysis, reduced dispersion/deflocculation, reduced corrosion inhibition, etc. The consequence of the inventive action of the peroxide activator/stabilizer and the hydrolysis-stable, organic sequestrant based on phosphonic acid, as well as the elimination of the hydrolysis-sensitive, inorganic polyphosphates ensure that the cleaning tablet of the present invention does not suffer from the above disadvantages. It is also fully effective from ambient temperature and does not require the warm water temperatures which have heretofore been necessary. There is therefore no need for the user to worry about the cleaning and disinfecting action that will be obtained if the user does not follow the manufacturer's instructions and use warm cleaning liquid.

It has not heretofore been possible with known cleaning tablets to monitor in a sensory or visual manner the sequence and end of the cleaning process. Even with the known two-layer tablets, merely a precleaning intermediate stage can be followed, whereas the end of the main and final cleaning is not made apparent to the user. The heretofore used colours of the tablets (e.g. blue, pink) are visible long after the end of the washing process when using glass vessels, even if another effect is really sought.

However, on using the proposed dye system of the present invention, the problems heretofore encountered with respect to the optical monitoring of the cleaning process can be eliminated. This involves the use of a redox-sensitive dye with a relatively weak oxidation potential combined with a different coloured dye independent of the redox potential. The protons freed through the oxidation of the contaminants and a certain proton delivery from the other tablet substances lead to a quantitative reduction in the dye intensity, followed by a qualitative colour change, before decolouring occurs. The timing sequence is dependent on the degree of contamination of the denture, as well as in part the temperature and pH-value of the water. It is possible to optically observe, in virtually all cases, the end of the main cleaning phase by the colour change, and the end of the cleaning process optimized for the intended action time by complete decolouring. This is realized according to the present invention by utilizing different appropriate colour systems. When using the present combination with indigotin disulphonic acid disodium salt and quinophthalone disulphonic acid disodium salt a turquoise green colour is obtained. The colour intensity decreases during the cleaning process and then changes to a greenish yellow (at the end of the main cleaning), before decolouring occurs (at the end of cleaning).

In an embodiment, the cleaning tablet according to the present invention can have the following components and composition ranges:

| | |
|---|---|
| Sodium perborate monohydrate | 15–30% by weight |
| Potassium monopersulphate | 20–40% by weight |
| Sodium hydrogen carbonate | 10–30% by weight |
| Sodium carbonate | 0–10% by weight |
| Sodium sulphate | 0–10% by weight |
| Citric acid or citrate salts and other similarly acting organic acids or their salts | 5–20% by weight |
| Tetraacetyl ethylenediamine and other similarly acting peroxide activators | 0.3–3% by weight |
| Organic phosphonic acid or its salts | 0.5–3% by weight |
| Polyethyleneglycol 20,000 | 1–4.5% by weight |
| Polyvinylpyrrolidone | 0–3% by weight |
| Silicon dioxide (Aerosil 200/300) | 0.5–1.5% by weight |
| Sodium dodecyl benzene sulphonate ricinyl monoethanol amide sulphosuccinate, disodium salt or similarly acting surfactants | 0.2–1.5% by weight |
| Hardened triglycerides | 0–2% by weight |
| Fatty alcohol polyglycol ethers | 0.5–2% by weight |
| Preservatives/stabilizers | 0–2% by weight |
| Peppermint powder or other aromatizing substances (e.g. eucalyptus) | 1–2% by weight |
| Dye system (e.g. indigotin L-Blue 2 and quinoline yellow L-yellow 3) | 0.05–0.35% by weight |

By way of example, and not limitation, an example of the cleaning tablet of the present invention will now be given. The cleaning tablet, in an embodiment, has the following composition.

| | |
|---|---|
| 30% by weight | sodium perborate monohydrate |
| 20% by weight | potassium monopersulphate |
| 20% by weight | sodium hydrogen carbonate |
| 5% by weight | sodium carbonate |
| 4% by weight | sodium sulphate |
| 7% by weight | citric acid, sodium salt |
| 1.5% by weight | tetraacetyl ethylene diamine |
| 1.5% by weight | organic phosphonic acids or their salts |
| 4% by weight | polyethyleneglycol 20,000 |
| 1.5% by weight | polyvinylpyrrolidone |
| 1.5% by weight | Aerosil 200/300 |
| 0.75% by weight | sodium dodecyl benzene sulphonate |
| 0.5% by weight | hardened triglycerides |
| 1% by weight | fatty alcohol polyglycol ether |
| 1% by weight | preservative |
| 0.5% by weight | peppermint powder |
| 0.25% by weight | indigotin L-blue 2 and quinoline yellow L-yellow 3. |

The above constituents were pressed into a powder or a granulated form using known methods to form a cleaning tablet. After dissolving, the resulting cleaning tablet had a pH-value in the cleaning liquid of 9.0, at a temperature of the latter of 30° C. It was possible to optically follow the course of the cleaning process by a corresponding colour change and was completed after roughly 10 minutes.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A cleaning tablet for the automatic cleaning of dentures in an aqueous solution, including at least one compound chosen from the group consisting of: sodium carbonate and carbonates in an amount of approximately 10 to about 40 percent by weight, at least one compound chosen from the group consisting of: citric acid, citrate, and citrates in an amount of approximately 5 to about 20 percent by weight, sodium perborate in an amount of approximately 15 to about 30 percent by weight, potassium monopersulphate in an amount of approximately 10 to about 40 percent by weight, and including a content of surfactants and foam forming agents, binders, lubricants and disintegrants, antimicrobial agents, carriers, flavouring/aromatizing substances, and at least one perborate/peroxide activator and at least one phosphorus compound; the activator content being between approximately 0.5 to about 3.0% by weight of the total composition of the cleaning tablet, the phosphorus compound being exclusively at least one compound chosen from the group consisting of hydrolysis-stable organic phosphonic acid and salts thereof functioning as a stabilizing agent and being present in a content of between approximately 0.5 to about 3.0% by weight of the total composition of the cleaning tablet and the total composition of the cleaning tablet being free of any hydrophobic binder and being free from inorganic phosphates/polyphosphates and organic sequestrants based on aminocarboxylic acids.

2. The cleaning tablet of claim 1, wherein tetraacetyl ethylene diamine (TAED) is used as an activator.

3. The cleaning tablet of claim 1 wherein a pH-value of a cleaning liquid produced by dissolving the cleaning tablet in water is between approximately 7.6 to about 9.6.

4. The cleaning tablet of claim 1 wherein the phosphorus compound content of the total cleaning tablet composition is between approximately 0.5 to about 2.5% by weight.

5. The cleaning tablet of claim 1 wherein the tablet includes a dye system having at least two dyes, at least one of the dyes being present in a keto-form coloured with chromophoric groups and as a result of hydrogen ions released during cleaning with the tablet, changes into a colourless, desmotropic leucoenol form, and at least one of the dyes is a redox-neutral.

6. The cleaning tablet of claim 5 wherein the dye system includes a combination of sodium-indigotin disulphonate and sodium quinophthalone disulphonate.

7. The cleaning tablet of claim 5 wherein the content of the dye system with respect to the total composition of the cleaning tablet is between approximately 0.5 to about 0.35% by weight.

8. The cleaning tablet of claim 5 wherein the phosphorus compound content of the cleaning tablet composition is between approximately 0.5 to about 2.5% by weight.

9. A cleaning tablet for the automatic cleaning of dentures in an aqueous solution, including at least one compound chosen from the group consisting of sodium carbonate, and carbonates, in an amount of approximately 10 to about 40 percent by weight, at least one compound chosen from the group consisting of citric acid, citrate, and citrate, in an amount of approximately 15 to about 30 percent by weight monopersulphate in an amount of approximately 20 to about 40 percent by weight, and including a content of surfactants and foam forming agents, binders, lubricants and disintegrants, antimicrobial agents, carriers, aromatizing/flavouring substances, and including, a dye system having at least two dyes, at least one dye being present in a keto-form coloured with chromophoric groups and as a result of hydrogen ions released during cleaning with the cleaning tablet changes into a colourless, desmotropic leucoenol form, and at least one of the dyes is a redox-neutral.

10. The cleaning tablet of claim 3, wherein the dye system includes a combination of sodium-indigotin disulphonate and sodium quinophthalone disulphonate.

11. The cleaning tablet of claim 3 wherein the dye system content with respect to the total composition of the cleaning tablet is between approximately 0.05 to about 0.35% by weight.

12. The cleaning tablet of claim 3 wherein the pH-value of a cleaning liquid produced by dissolving the cleaning tablet in water is between approximately 7.6 to about 9.6.

13. The cleaning tablet of claim 3 wherein the cleaning tablet has a multilayer structure.

14. A composition for cleaning dentures in an aqueous solution comprising:
   at least one compound chosen from the group consisting of sodium hydrogen carbonate, sodium carbonate, and carbonates in an amount of approximately 10 to about 40 percent by weight;
   a least one compound chosen from the group consisting of citric acid, citrate, and citrates in an amount of approximately 5 to about 20 percent by weight;
   sodium perborate in an amount of approximately 15 to about 30 percent by weight;
   potassium monopersulphate in an amount approximately 20 to about 40 percent by weight;
   at least one perborate/peroxide activator in a content of approximately 0.5 to about 3.0 percent by weight of the total composition;
   at least one compound chosen from the group consisting of hydrolysis - stable organic phosphonic acid and salts thereof, being present in a content of approximately 0.5 to about 3.0 percent by weight of the total composition;
   a dye system including a keto-form coloured dye with chromophic groups and a redox-neutral dye; and
   the composition is free of any hydrophobic binders and does not include inorganic phosphates and organic sequestrants based on amino carboxylic acids.

15. The cleaning composition of claim 14 wherein tetraacetyl ethylene diamine is used as an activator.

16. The cleaning composition of claim 14 wherein the dye system includes a combination of sodium-indigotin disulphonate and sodium quinophthalone disulphonate.

17. The cleaning composition of claim 14 wherein the dye system content with respect to the total composition of the cleaning tablet is between approximately 0.05 to about 0.35% by weight.

18. The cleaning composition of claim 14 wherein a pH-value of a cleaning liquid produced by dissolving the cleaning tablet in water is between approximately 7.6 to about 9.6.

* * * * *